(12) United States Patent
Shang

(10) Patent No.: US 10,092,209 B2
(45) Date of Patent: *Oct. 9, 2018

(54) NON-INVASIVE IN SITU GLUCOSE LEVEL SENSING USING ELECTROMAGNETIC RADIATION

(71) Applicant: Advantest Corporation, Tokyo (JP)

(72) Inventor: Yang Shang, San Jose, CA (US)

(73) Assignee: ADVANTEST CORPORATION, Tokyo (JP)

( * ) Notice: Subject to any disclaimer, the term of this patent is extended or adjusted under 35 U.S.C. 154(b) by 369 days.

This patent is subject to a terminal disclaimer.

(21) Appl. No.: 14/808,409

(22) Filed: Jul. 24, 2015

(65) Prior Publication Data

US 2016/0095540 A1   Apr. 7, 2016

Related U.S. Application Data

(60) Provisional application No. 62/059,702, filed on Oct. 3, 2014.

(51) Int. Cl.
*A61B 5/1455* (2006.01)
*A61B 5/05* (2006.01)
*A61B 5/145* (2006.01)
*A61B 5/00* (2006.01)

(52) U.S. Cl.
CPC ......... *A61B 5/0507* (2013.01); *A61B 5/1455* (2013.01); *A61B 5/14507* (2013.01); *A61B 5/14532* (2013.01); *A61B 5/68* (2013.01); *A61B 5/6821* (2013.01); *A61B 2560/0223* (2013.01); *A61B 2560/0425* (2013.01); *A61B 2560/0431* (2013.01)

(58) Field of Classification Search
CPC ............. A61B 5/1455; A61B 5/14532; A61B 5/14558

See application file for complete search history.

(56) References Cited

U.S. PATENT DOCUMENTS

| | | | | |
|---|---|---|---|---|
| 5,209,231 A | * | 5/1993 | Cote | A61B 5/14558 600/310 |
| 5,535,743 A | * | 7/1996 | Backhaus | A61B 5/14558 600/310 |
| 6,704,588 B2 | * | 3/2004 | Ansari | A61B 5/14532 600/319 |
| 7,684,044 B2 | * | 3/2010 | Sekiguchi | G01N 21/3581 356/445 |
| 8,207,501 B2 | * | 6/2012 | Katagiri | G01J 3/42 250/341.1 |
| 2016/0095533 A1 | | 4/2016 | Shang | |

* cited by examiner

*Primary Examiner* — Eric Winakur

(57) ABSTRACT

System and method of using electromagnetic radiation signals to non-invasively test a glucose level in a subject. During operation, an incident beam of Terahertz waves is generated and projected onto the surface of the eyeball, which is naturally reflected by a tear layer. The reflected Terahertz waves are detected and characterized to determine the reflection characteristics of the tear layer, e.g., an axial ratio of reflection coefficients in two polarization orientations. Provided with the determined axial ratio and according to a predetermined correlation among axial ratio, tear glucose level and blood glucose level, the current blood glucose level in the subject can be derived and presented to a user.

19 Claims, 11 Drawing Sheets

NON-INVASIVE IN SITU GLUCOSE LEVEL SENSING USING ELECTROMAGNETIC RADIATION

CROSS REFERENCE

This patent application claims priority to the U.S. provisional patent application No. 62/059,702, filed on Oct. 3, 2014, titled "NON-INVASIVE IN SITU GLUCOSE LEVEL SENSING," the entire content of which is herein incorporated by reference for all purposes.

TECHNICAL FIELD

The present disclosure relates generally to the field of blood glucose level sensing, and more particularly, to non-invasive glucose level sensing mechanisms.

BACKGROUND

People suffering from diabetes have abnormally high levels of blood sugar or blood glucose because of inadequate production of insulin by the body or the body's incapability of properly responding to the present insulin.

Diabetes is generally considered incurable and regular monitoring and controlling of blood sugar level is a major part of the treatment. Patients with diabetes control their blood sugar levels through medication, diet and exercise, and in some cases insulin injections. Patients often need to monitor their own blood sugar levels at home on a daily basis to ensure effectiveness of the treatment regime.

Today's technology allows blood tests to be performed by patients at home using a portable test kit commonly called a glucose meter. To use the meter, a patient draws a blood sample by using a lancing device to prick a finger, applies the blood on a test strip inserted into the glucose meter. The glucose meter automatically performs analysis on the blood on the test strip and shows the glucose level readout in a display panel on the meter.

Because the lancing devices and test strips for a glucose meter are typically designed as disposable, the expense of using such a glucose meter can be a substantial economic burden. For instance, some patients need to test up to 5 times a day and thus use at least 5 lancets and 5 test strips, which can cost $600-1500 per year for each individual depending on the prices of the test strips and lancets. Besides the economic waste, disposable lancing devices and test strips are also a significant source of medical waste hazards and contribute to environmental contamination. In addition, pricking fingers or alternative sites to draw blood samples inflict physical discomfort and pain. Patients often feel the testing processes unpleasant and burdensome.

There have been recent developments in using non-invasive approaches to monitor and test glucose levels in patients. Studies have shown that human tear liquid also contains glucose, albeit in a diluted concentration compared to the blood. Human eyes are constantly lubricated and covered by a tear layer, and an elevated blood glucose level results in an elevated tear glucose level. Thus, instead of directly testing glucose contained in blood samples, there has been reported research in using contact lens built with on-lens electrochemical sensors and integrated circuitry to test glucose levels in tear liquid.

While this approach transforms the blood glucose test to a non-invasive nature, it requires patients to wear contact lens, which is still considered inconvenient and cumbersome to many patients.

SUMMARY OF THE INVENTION

Therefore, it would be advantageous to provide a non-invasive blood glucose testing mechanism that offers improved patient convenience without generating disposable medical waste.

Embodiments of the present disclosure employ controlled electromagnetic waves to irradiate a subject's eyeball and thereby determine a glucose level in the subject based on a known relationship between glucose level and reflection characteristics of the tear layer covering the eyeball with respect to the incident waves. During operation, an incident beam of electromagnetic waves with known characteristics, preferably in the Terahertz band, is generated and projected onto the surface of the eyeball, which is naturally reflected by the tear layer. The reflected electromagnetic waves are detected and characterized to determine the reflection characteristics of the tear layer, e.g., an axial ratio of reflection coefficients in two polarization orientations. Provided with the determined axial ratio and according to a predetermined correlation among: axial ratio; tear glucose level; and blood glucose level, the current blood glucose level in the subject can be derived and presented to a user, e.g., the subject or an individual conducting the testing on the subject.

In some embodiments, a glucose sensing device according to the present disclosure is designed as a handheld device for home use and can be placed against a user's forehead when in use. The sensing device includes a Terahertz wave transmitter and receiver, an eye position alignment system, a calibration system and processing logic. The eye alignment system facilitates a user to adjust the eyeball position relative to the device to achieve the predetermined angle of incidence and predetermined distances among the transmitter, the receiver and the eyeball for optimal test results. The calibration system utilizes a reference surface having known reflection characteristics with respect to the incident beam. The transmitter can emit a beam of electromagnetic wave to the eyeball surface with electrical fields in two polarization orientations; the receiver can determine the electrical fields in two polarization orientations of reflected beam. The processing logic performs analysis and calculations to determine the reflection characteristics of the tear layer based on the electric fields of the incident and reflected beams, and accordingly outputs a blood glucose level result.

Because a blood glucose level can be inferred from the reflection characteristics of the tear fluid present in the subject's eyeball with respect to non-invasive electromagnetic waves, patients can be advantageously relieved from the conventional and painful blood sampling processes. In addition, the sensing device beneficially utilizes no disposable medical supplies and generates no medical waste.

According to one embodiment of the present disclosure, a method of determining a glucose levels includes irradiating first electromagnetic waves onto an eyeball of a subject and detecting second electromagnetic waves produced by the first electromagnetic waves being reflected from the eyeball. The glucose level in the subject is automatically determined based on characteristics of the first electromagnetic waves and the second electromagnetic waves.

In one embodiment, the first electromagnetic waves and the second electromagnetic waves are Terahertz waves. The second electromagnetic waves originate by first electromagnetic waves reflecting from a tear film covering the eyeball. To determine the glucose level, an axial ratio is determined, which is a ratio between reflection coefficients of the tear film with respect to the first electromagnetic waves in two orthogonal polarization orientations. The glucose level is determined according to: a predetermined correlation between the axial ratio and a tear glucose level; and a predetermined correlation between the tear glucose level and a blood glucose level.

According to another embodiment of the present disclosure, a method of determining a glucose level in a subject includes: at a first predetermined position relative to an eyeball of the subject, irradiating first Terahertz waves onto the eyeball; and, at a second predetermined position relative to the eyeball, detecting second Terahertz waves produced by the first Terahertz waves being reflected from a tear layer covering the eyeball. The method further includes automatically determining the glucose level in the subject based on characteristics of the second Terahertz waves relative to the first Terahertz waves.

According to still another embodiment of the present disclosure, a method of detecting a glucose level of a subject includes: (1) irradiating first electromagnetic waves onto an eyeball of the subject; (2) determining reflection characteristics of a tear layer covering the eyeball with respect to the first electromagnetic waves; and (3) determining the glucose level in the subject based on the reflection characteristics of the tear layer with respect to the first electromagnetic waves.

This summary contains, by necessity, simplifications, generalizations and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

Embodiments of the present invention will be better understood from a reading of the following detailed description, taken in conjunction with the accompanying drawing figures in which like reference characters designate like elements and in which.

DETAILED DESCRIPTION

Figure 1:
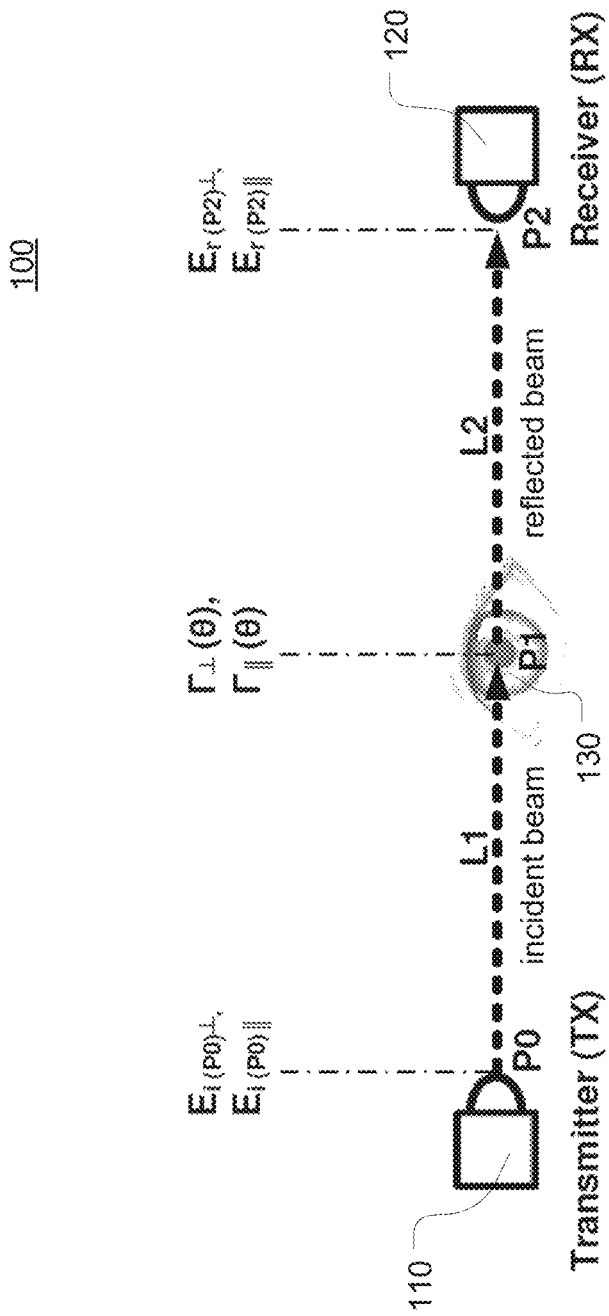
FIG. 1 illustrates the front view of the configuration of an exemplary glucose sensing device using electromagnetic radiation to test tear glucose levels according to an embodiment of the present disclosure.

Reference will now be made in detail to the preferred embodiments of the present invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail so as not to unnecessarily obscure aspects of the embodiments of the present invention. The drawings showing embodiments of the invention are semi-diagrammatic and not to scale and, particularly, some of the dimensions are for the clarity of presentation and are shown exaggerated in the drawing Figures. Similarly, although the views in the drawings for the ease of description generally show similar orientations, this depiction in the Figures is arbitrary for the most part. Generally, the invention can be operated in any orientation.

Notation and Nomenclature

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "processing" or "accessing" or "executing" or "storing" or "rendering" or the like, refer to the action and processes of a computer system, or similar electronic computing device, that manipulates and transforms data represented as physical (electronic) quantities within the computer system's registers and memories and other computer readable media into other data similarly represented as physical quantities within the computer system memories or registers or other such information storage, transmission or client devices. When a component appears in several embodiments, the use of the same reference numeral signifies that the component is the same component as illustrated in the original embodiment.

Non-Invasive In Situ Glucose Level Sensing Using Electromagnetic Radiation

Provided herein are systems and methods of using electromagnetic signals to non-invasively test a glucose level in the tear liquid covering a subject's eyeball surface and thereby inferring a blood glucose level in the subject. An exemplary glucose sensing device includes an electromagnetic wave transmitter, a wave detector and processing logic. A correlation between tear glucose level and blood glucose level of the subject as well as the interaction pattern between a tear layer and the testing electromagnetic waves is acquired beforehand and used to configure the sensing device. During testing, controlled electromagnetic waves are generated by the transmitter and projected onto the eyeball. The waves reflected from the eyeball surface are detected by the wave detector. The reflection characteristics of the tear liquid are determined based on the analysis on the reflected waves and then related to the blood glucose level in the subject.

Because a blood glucose level can be inferred from the reflection characteristics of the tear present in the subject's eyeball with respect to non-invasive electromagnetic waves, patients can be advantageously relieved from the conventional and painful blood sampling process. In addition, the detection process and device beneficially utilizes no disposable medical supplies and generates no medical waste. Moreover, embodiments of the present disclosure advantageously do not rely on tactile contact between any external object and a sensitive part of a human body (as does in the contact lens approach discussed above), which further enhances user convenience and experience.

Although the present disclosure is not limited by the spectrum of the testing electromagnetic waves or signals, Terahertz waves are preferred due to the attributes of being non-ionizing and so safe to human tissue, highly sensitive to water hydration and sugar concentrations, and highly directional at low energy. For example, the Terahertz waves used for glucose testing may have a frequency within the range of 100 GHz to 10 THz in one embodiment. However, other suitable classes of electromagnetic radiation may also be used for sensing tear glucose levels without departing from the scope of the present disclosure.

Figure 2:
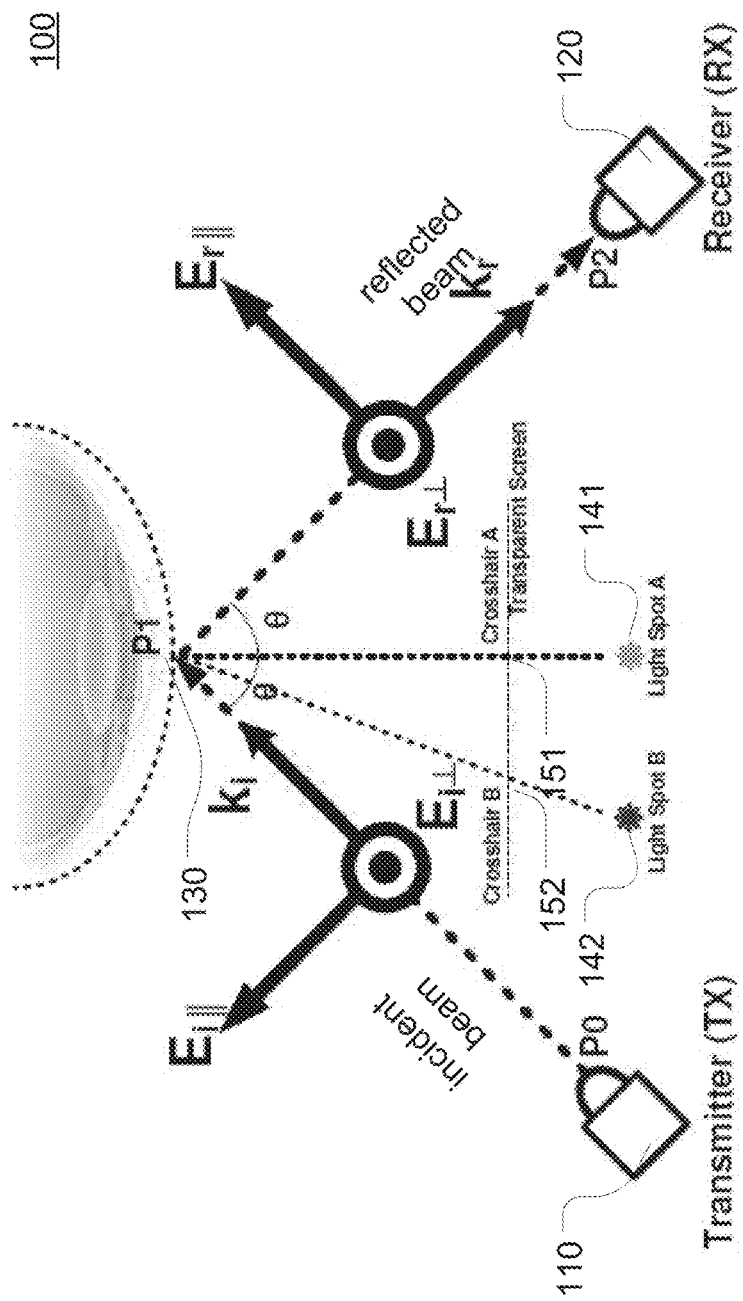
FIG. 2 illustrates the top view of the configuration of the exemplary glucose sensing device as shown in FIG. 1.
Figure 3:
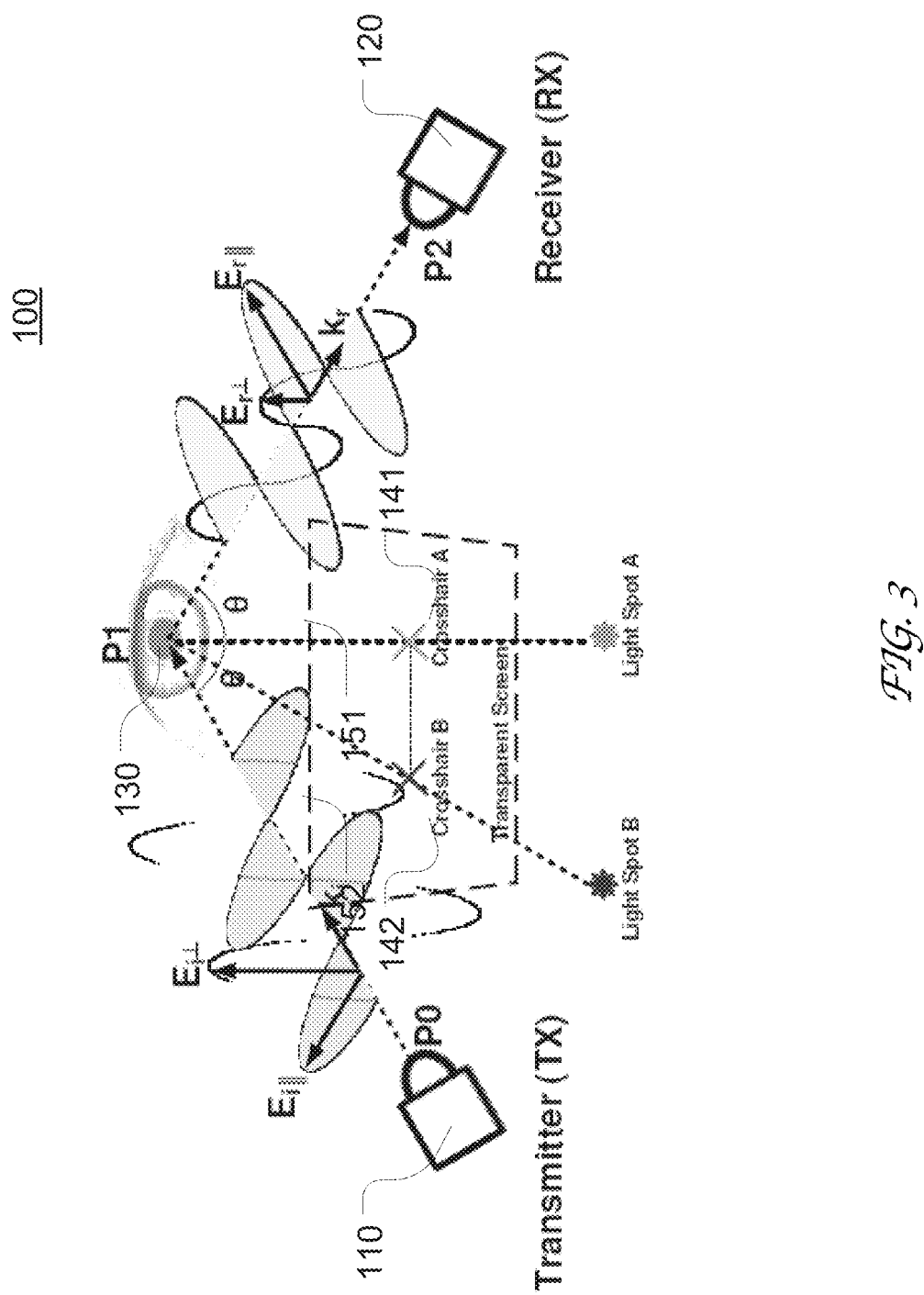
FIG. 3 illustrates the perspective view of the exemplary glucose sensing device as shown in FIG. 1 and FIG. 2.

FIG. 1 illustrates the front view of the configuration of an exemplary glucose sensing device 100 using electromagnetic radiation to test tear glucose level according to an embodiment of the present disclosure. FIG. 2 illustrates the top view of the configuration of the exemplary glucose sensing device 100 as shown in FIG. 1. FIG. 3 illustrates the 3D view of the exemplary glucose sensing device 100 as shown in FIGS. 1 and 2.

The configuration is illustrated in a basic form and includes a transmitter (TX) 110 and a receiver (RX) 120 of Terahertz waves disposed at locations P0 and P2, respectively. During operation, the transmitter generates and directs a beam of Terahertz radiation to the eyeball surface 130 of a subject at location P1. The incident beam travels a distance L1 until it is reflected by the eyeball surface 130 at P1 which is covered by a tear layer. The reflected beam is detected by the receiver 120 at a distance L2 from the reflection point P1.

As described in greater detail below, the glucose sensing device 100 includes a position alignment system serving to facilitate a user to adjust the eyeball position until the angle of incidence θ and the distances L1 and L2 equal to predetermined values.

The glucose levels in tear fluid are reported to be in the range of 0.1-0.6 millimoles per liter (mM), which is about ten times lower than the levels in the blood. A device according to an embodiment of the present disclosure is configured to offer accurate measurement in this range.

It is appreciated that the reflection properties of the eyeball vary with the biochemical composition, and particularly the glucose concentration, in the tear. In the embodiments described in detail herein, cross polarized reflectance measurements are used for Terahertz radiology analysis in the testing and calibration processes, which eliminate the dependency on knowledge of emitted power, path loss and other parameters and the characteristics of the emitted beam.

More specifically, the reflection coefficients in two orientations (in-plane $\Gamma_\|(\theta)$ and normal $\Gamma_\perp(\theta)$) or a ratio thereof is used as the metrics indicating the tear glucose level, where θ represents an angle of incidence. To obtain $\Gamma_\|(\theta)$ and $\Gamma_\perp(\theta)$, the electric fields (E-fields) of the incident beam as generated at P0 ($E_{i(P0)}^\perp$ and $E_{i(P0)}^\|$) and the E-fields of the reflected beam as detected at P2 ($E_{r(P2)}^\perp$ and $E_{r(P2)}^\|$) are determined.

As shown in FIGS. 1-3, the E-fields detected by the receiver is a function of the E-fields generated by the transmitter, the distance between the transmitter (P0) and the reflection point (P1) on the eye 130, the reflection coefficients of the tear surface at P0, and the distance between P1 and the receiver (P2). This relation can be expressed as following:

$$\begin{cases} E_{r(P2)\perp} = E_{i(p0)\perp} \cdot L_{L1} \cdot \Gamma_\perp(\theta) \cdot L_{L2}; & (1) \\ E_{r(P2)\|} = E_{i(p0)\|} \cdot L_{L1} \cdot \Gamma_\|(\theta) \cdot L_{L2}; & (2) \\ \Gamma_\perp(\theta) = \dfrac{E_{r(P1)\perp}}{E_{i(P1)\perp}}; & (3) \\ \Gamma_\|(\theta) = \dfrac{E_{r(P1)\|}}{E_{i(P1)\|}}. & (4) \end{cases}$$

where the variables in Equation (1) are defined as follows:

$\begin{cases} E_{i(P0)\perp}: & \text{Indicent } E-\text{field normal to the plane of incidence at } P0; \\ E_{i(P0)\|}: & \text{Indicent } E-\text{field parallel to the plane of incidence at } P0; \\ E_{i(P1)\perp}: & \text{Indicent } E-\text{field normal to the plane of incidence at } P1; \\ E_{i(P1)\|}: & \text{Indicent } E-\text{field parallel to the plane of incidence at } P1; \\ E_{r(P1)\perp}: & \text{Reflected } E-\text{field normal to the plane of incidence at } P1; \\ E_{r(P1)\|}: & \text{Reflected } E-\text{field parallel to the plane of incidence at } P1; \\ E_{r(P2)\perp}: & \text{Reflected } E-\text{field normal to the plane of incidence at } P2; \\ E_{r(P2)\|}: & \text{Reflected } E-\text{field parallel to the plane of incidence at } P2; \\ \Gamma_\perp(\theta): & \text{Reflection coefficients at } P1 \text{ for normal polarization}; \\ \Gamma_\|(\theta): & \text{Reflection coefficients at } P1 \text{ for parallel polarization}; \\ L_{L1}: & \text{Path loss from } P0 \text{ to } P1; \\ L_{L2}: & \text{Path loss from } P1 \text{ to } P2; \\ \theta: & \text{Incidence angle}. \end{cases}$ The axial ratio ($AR_\Gamma(\theta)$) between reflection coefficients $\Gamma_\perp(\theta)$ and $\Gamma_\|(\theta)$ is defined as:

$$AR_\Gamma(\theta) = \left| \frac{\Gamma_\perp(\theta)}{\Gamma_\|(\theta)} \right| \qquad (5)$$

Using Fresnel's equations, it is obtained that $$\begin{cases} \Gamma_\perp(\theta) = \dfrac{n_A \cos\theta - n_T \sqrt{1 - \left(\frac{n_A}{n_T} \sin\theta\right)^2}}{n_A \cos\theta + n_T \sqrt{1 - \left(\frac{n_A}{n_T} \sin\theta\right)^2}} \\ \\ \Gamma_\|(\theta) = \dfrac{n_A \sqrt{1 - \left(\frac{n_A}{n_T} \sin\theta\right)^2} - n_T \cos\theta}{n_A \sqrt{1 - \left(\frac{n_A}{n_T} \sin\theta\right)^2} + n_T \cos\theta} \end{cases} \qquad (6)$$

where $n_A$ and $n_T$ are the refractive indexes of air and tear, respectively. Refractive index $\tilde{n}$ can be represented in a complex form, i.e., $\tilde{n}=n+jk$, where n and k indicate the phase velocity and the absorption loss, respectively.

By substituting (6) into (5), it is obtained that $$AR_\Gamma(\theta) = \left| \frac{\left[n_A\cos\theta - n_T\sqrt{1-\left(\frac{n_A}{n_T}\sin\theta\right)^2}\right] \cdot \left[n_A\sqrt{1-\left(\frac{n_A}{n_T}\sin\theta\right)^2} + n_T\cos\theta\right]}{\left[n_A\sqrt{1-\left(\frac{n_A}{n_T}\sin\theta\right)^2} - n_T\cos\theta\right] \cdot \left[n_A\cos\theta + n_T\sqrt{1-\left(\frac{n_A}{n_T}\sin\theta\right)^2}\right]} \right| \quad (7)$$

If $n_A$ is approximated as unity, Equation (7) can be simplified as $$AR_\Gamma(\theta) = \left| \frac{\cos\theta \cdot \sqrt{1-\left(\frac{\sin\theta}{n_T}\right)^2} + \frac{\sin^2\theta}{n_T}}{\cos\theta \cdot \sqrt{1-\left(\frac{\sin\theta}{n_T}\right)^2} - \frac{\sin^2\theta}{n_T}} \right| \quad (8)$$

Figure 4:
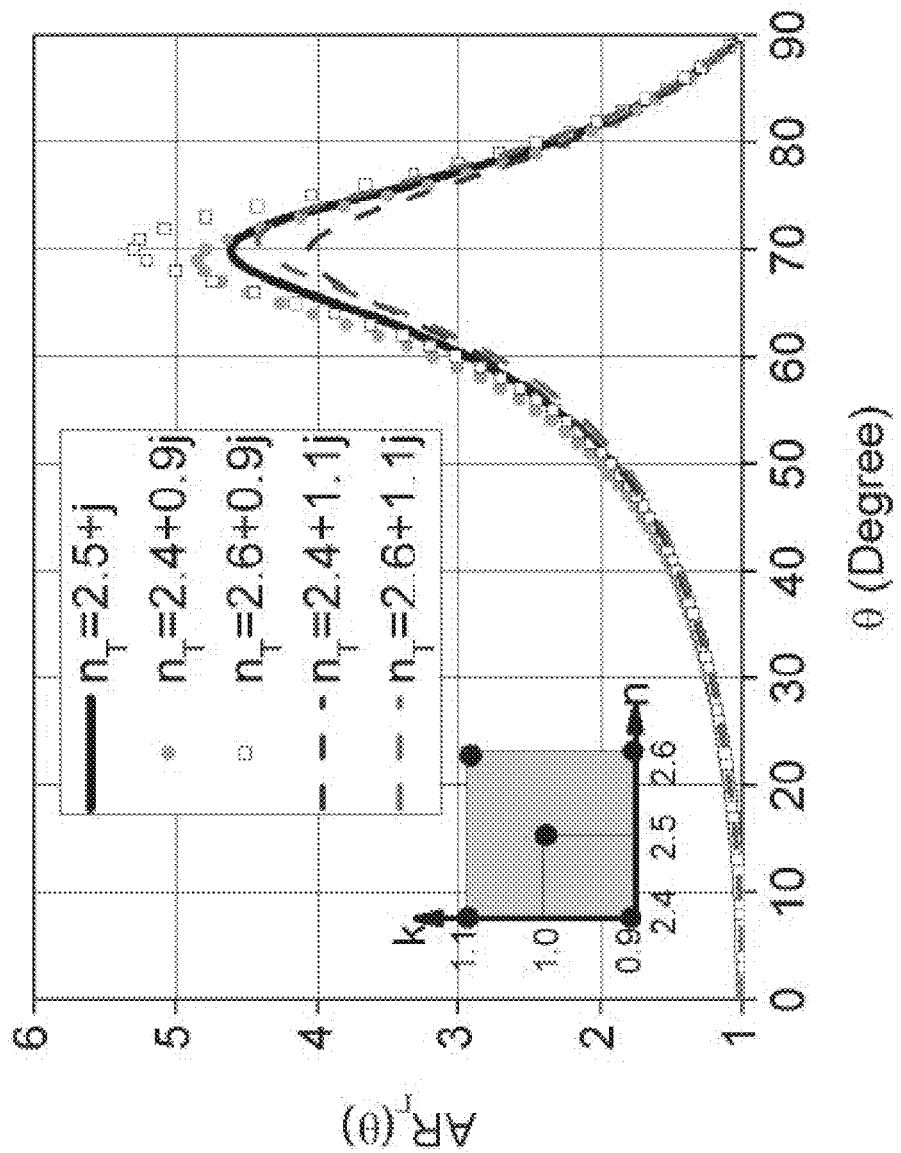
FIG. 4 shows simulated data plots of $AR_T$ as a function of angle of incidence in various refractive indexes which may be caused by different glucose concentrations in tear fluid.

According to Equation (8), $AR_\Gamma(\theta)$ is a function of $n_T$ and $\theta$. For a typical tear sample $n_T$=2.5+j. FIG. 4 shows simulated data plots of $AR_\Gamma$ as a function of angle of incidence in various refractive indexes which may be caused by different glucose concentrations in tear. FIG. 4 demonstrates that $AR_\Gamma$ varies with the refractive index of the tear.

Figure 5:
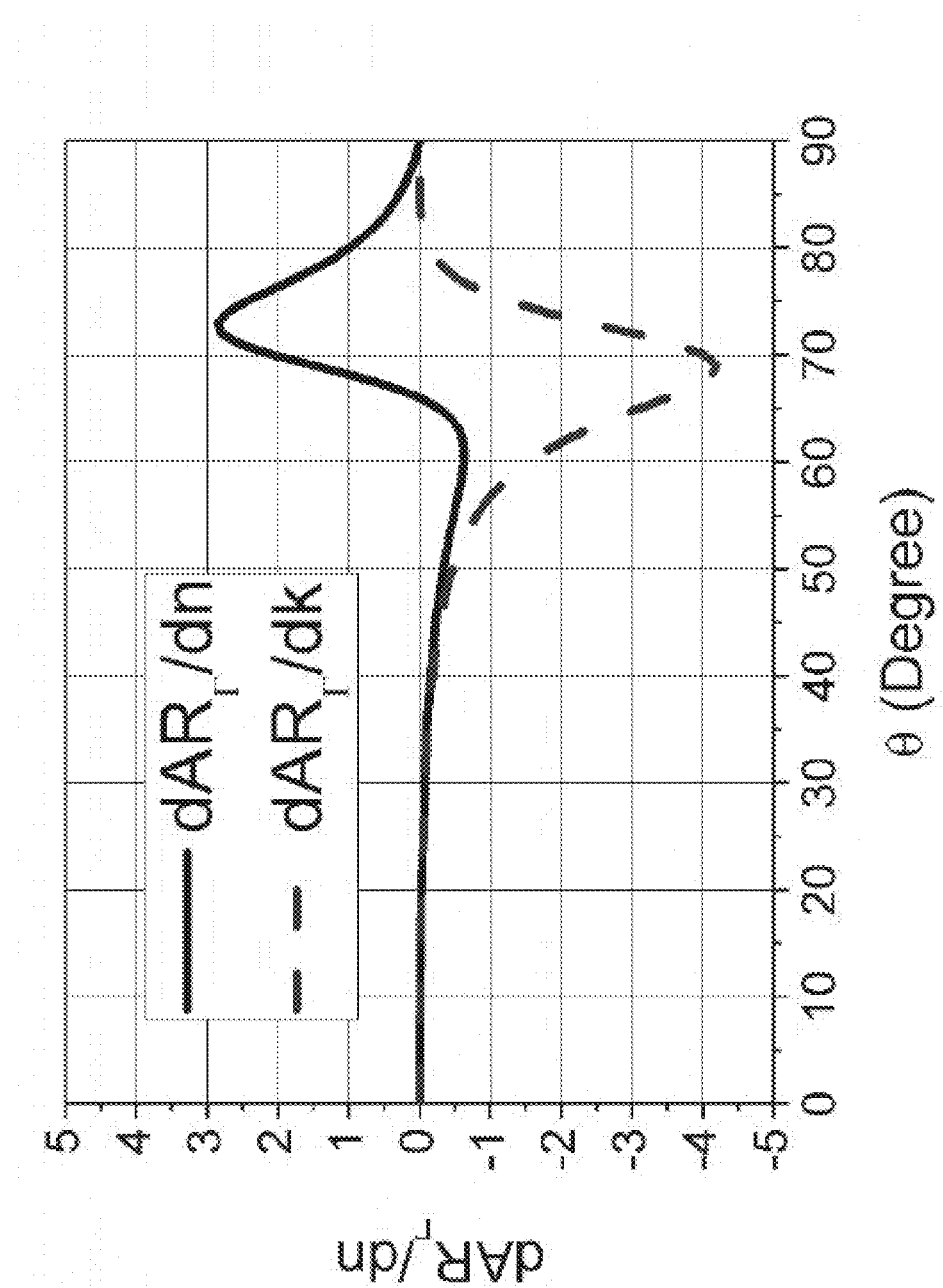
FIG. 5 are data plots showing the derivatives of $AR_T(\theta)$ of n and k with $n_T$ equal to 2.5+j.

Since that the variation of $n_T$ is correlated to the glucose level in the tear, a glucose level can be obtained by the measurement of $n_T$. FIG. 5 are data plots showing the derivatives of $AR_\Gamma(\theta)$ of n and k with $n_T$ equal to 2.5+j. FIG. 5 demonstrates that an incidence angle between 55 and 85 degrees yields the high sensitivity in the detection of $n_T$ by the measurement of $AR_\Gamma$. In practice, the incidence angle may be selected from this high sensitivity region as a predetermined value for configuring a glucose sensing device, as described in greater detail below.

By substituting Equation (1) and (2) into (5), $AR_\Gamma$ can be expressed as:

$$AR_\Gamma(\theta_0) = \frac{\Gamma_\perp(\theta_0)}{\Gamma_\parallel(\theta_0)} = \frac{E_{r(P2)\perp} \cdot E_{i(p0)\parallel}}{E_{r(P2)\parallel} \cdot E_{i(p0)\perp}} \quad (9)$$

where $\theta_0$ is an optimum incidence angle selected to obtain a highest sensitivity in tear glucose level detection. In Equation (9), both $E_{r(P2)\perp}$ and $E_{r(P2)\parallel}$ can be directly measured on the receiver side; $E_{i(p0)\parallel}/E_{i(p0)\perp}$ can be obtained based on the operation settings of the transmitter (e.g., the power and frequency of the incident waves etc.). Alternatively $E_{i(p0)\parallel}/E_{i(p0)\perp}$ are obtained through a calibration process using reference mirror measurement.

Figure 6:
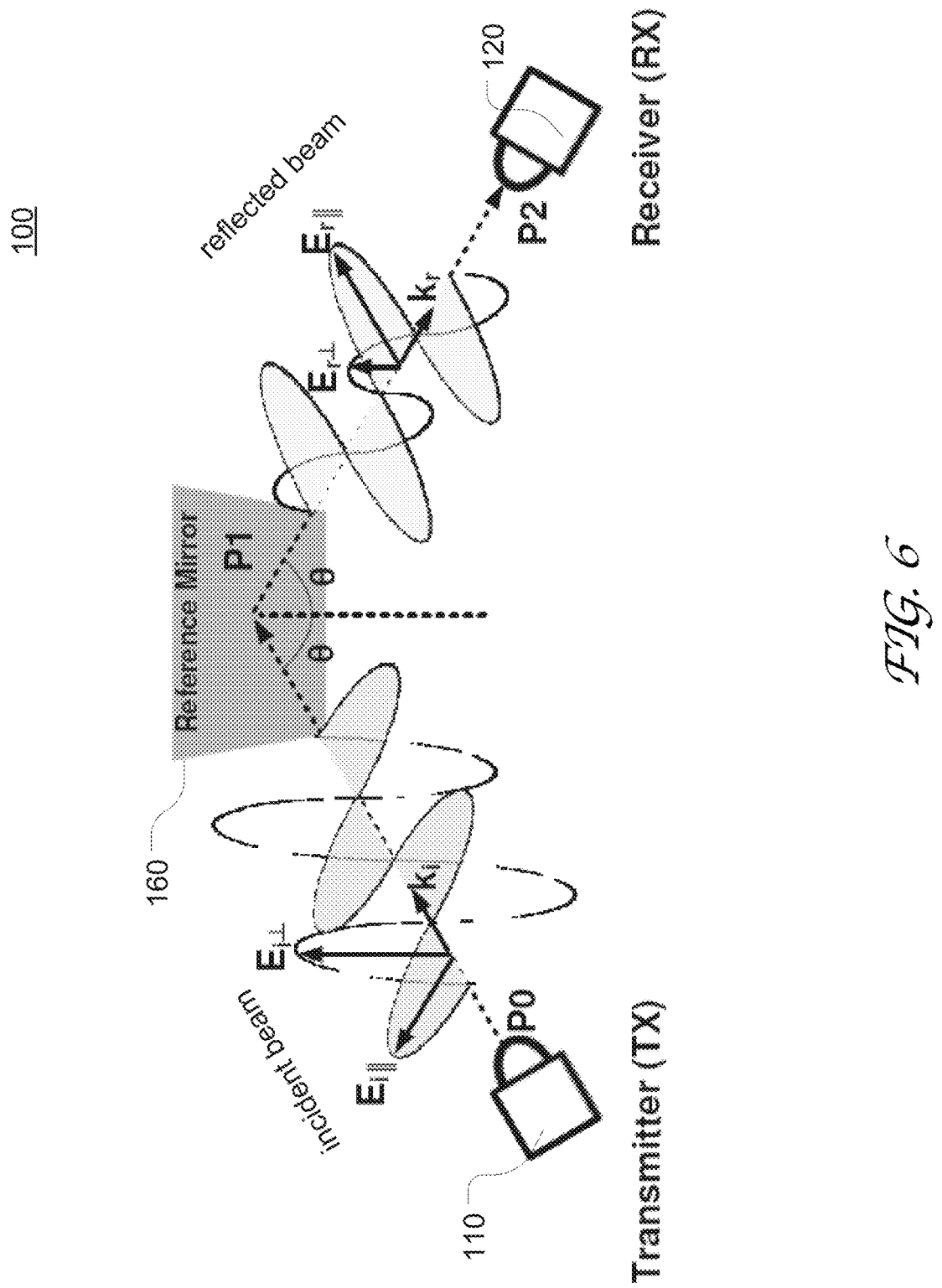
FIG. 6 illustrates the configuration of using a reference mirror to calibrate the exemplary glucose sensing device as shown in FIGS. 1-3 according to an embodiment of the present disclosure.

FIG. 6 illustrates the configuration of using a reference mirror to calibrate the exemplary glucose sensing device 100 as shown in FIGS. 1-3 according to an embodiment of the present disclosure. Herein, a reference mirror refers to a surface with high conductivity and its axial ratio of reflection is a known constant value $AR_{\Gamma,Mirror}(\theta_0)$. An example of such a reference mirror is a metal surface with k≈1. As such, $E_{i(p0)\parallel}/E_{i(p0)\perp}$ can be obtained from Equation (9):

$$\frac{E_{i(p0)\parallel}}{E_{i(p0)\perp}} = AR_{\Gamma,Mirror}(\theta_0) \cdot \frac{E_{r(P2)\parallel,Mirror}}{E_{r(P2)\perp,Mirror}} \quad (10)$$

where $E_{r(P2)\perp,Mirror}$ and $E_{r(P2)\parallel,Mirror}$ are the measured E-fields normal and parallel to the plane of incidence at P2 reflected from the reference mirror.

By substituting Equation (10) into (9), the tear axial ratio $AR_{\Gamma,Tear}(\theta_0)$ can be expressed by:

$$AR_{\Gamma,Tear}(\theta_0) = AR_{\Gamma,Mirror}(\theta_0) \frac{E_{r(P2)\perp,Tear} \cdot E_{r(P2)\parallel,Mirror}}{E_{r(P2)\parallel,Tear} \cdot E_{r(P2)\perp,Mirror}} \quad (11)$$

Thus, for each glucose test, the tear axial ratio $AR_{\Gamma,Tear}(\theta_0)$ can be calculated using Equation (11), where $E_{r(P2)\perp,Tear}$ and $E_{r(P2)\parallel,Tear}$ are the measured E-fields normal and parallel to the plane of incidence at P2 reflected from the tear film. In some embodiments, a glucose sensing device is configured such that the calibration process is performed periodically to ensure accurate test results.

Figure 7A:
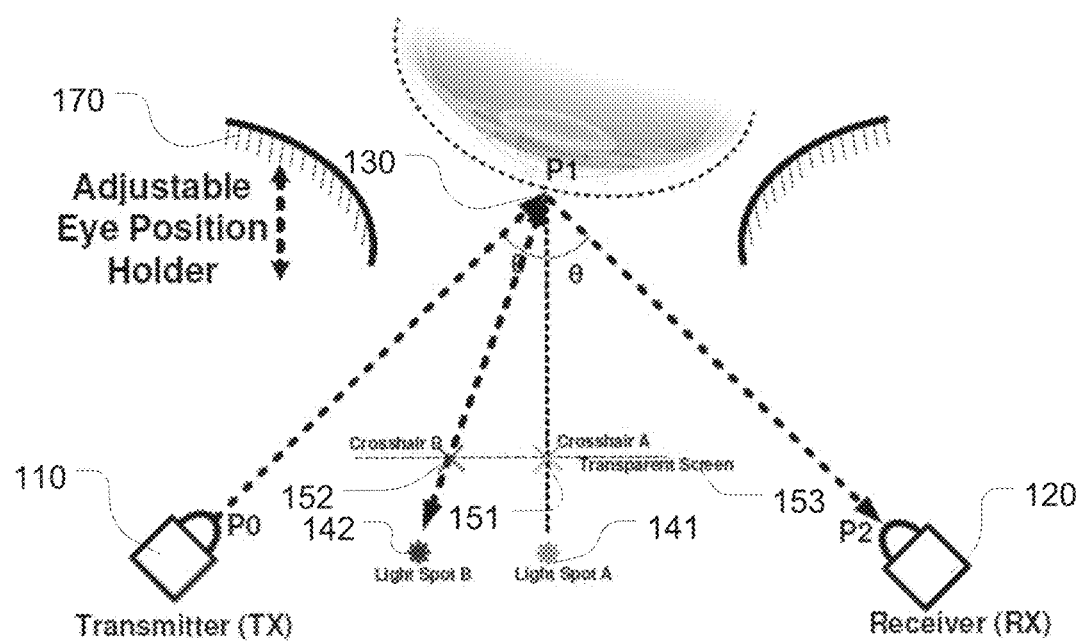
FIGS. 7A-7B show the configuration of using an exemplary positioning alignment system built in a glucose sensing device to achieve the predetermined angle of incidence $\theta_0$ and reflection position P1 for testing in accordance with an embodiment of the present disclosure.
Figure 7B:
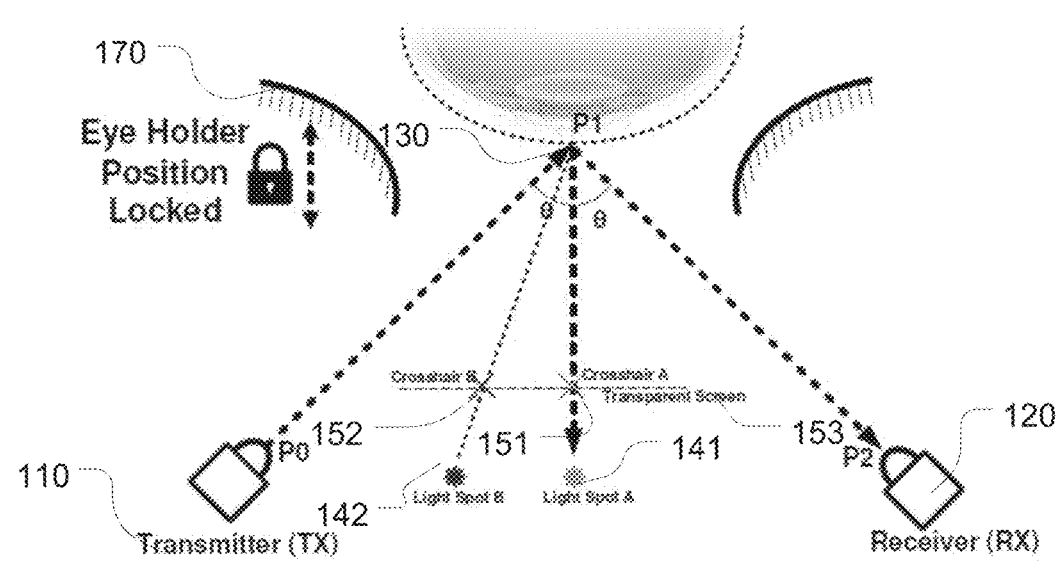

To use reference values of $E_{r(P2)\perp,Mirror}$ and $E_{r(P2)\parallel,Mirror}$ for computing an axial ratio, as in Equation (12), an eyeball under test should be consistently positioned at the same location each time as the reference mirror positioned in the calibration process. To this end, the glucose sensing device includes a position alignment system to facilitate positioning of the eyeball during glucose testing through an alignment process. FIGS. 7A-7B show the configuration of using an exemplary positioning alignment system built in the glucose sensing device 100 to achieve the predetermined angle of incidence $\theta_0$ and reflection position P1 for testing in accordance with an embodiment of the present disclosure. The position alignment system includes an adjustable eye position holder 170, light sources A 141 and B 142, and a viewfinder that can projects crosshairs A 151 and B 152 onto a transparent screen 153.

When performing self-alignment, e.g., before a test, a user looks through the viewfinder on the device 100 and adjusts the eye position holder 170 until he or she is able to visually align the light source B 142 with crosshair B 152 (as shown in FIG. 7A) and align the light source A 141 with crosshair A 151 (as shown in FIG. 7B). The pupil of the eyeball is an aperture which allows light into the eye and is almost centrally aligned with the eyeball. By aligning the pupil with the light sources and crosshairs, the correct positioning of the eyeball can be obtained, which ensures consistent measurements on the tear layer.

In some embodiments, the sensing device can send a confirmation indication that the eyeball is positioned correctly and ready for glucose test. Receiving the indication, the user can command to lock the eye holder 170 and activate the transmitter 110 along with other operational components for testing.

It will be appreciated that the present disclosure is not limited to any specific mechanism of determining the reflection characteristics of a tear layer with respect to incident radiation. For example, in some other embodiments, the current location of an eyeball may be automatically detected without relying on an alignment process. Also the E-fields of the incident and reflected beams may be directly determined based on the current eyeball location and without relying on a reference surface or the associated calibration process.

Figure 8:
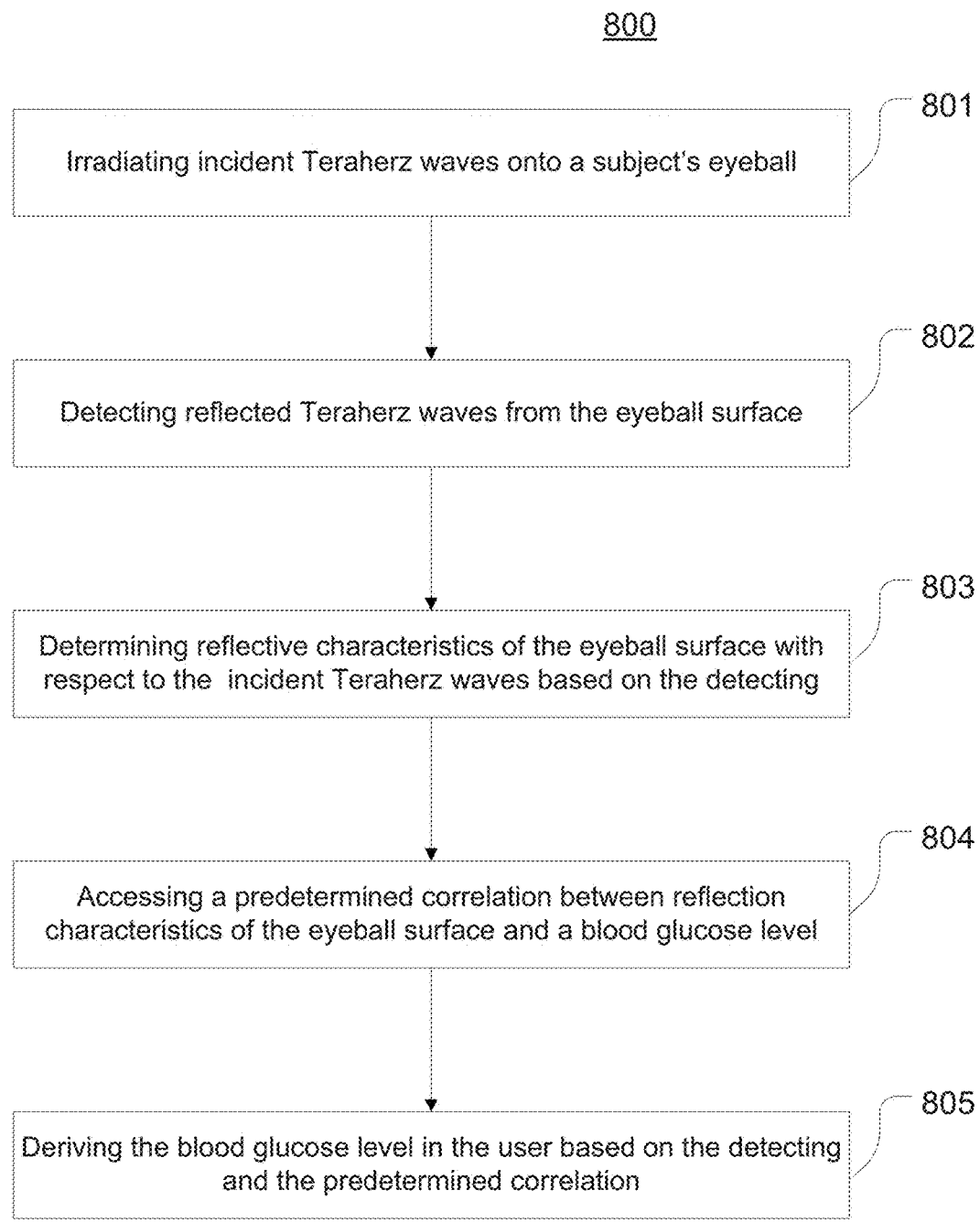
FIG. 8 is a flow chart depicting an exemplary process of using Terahertz waves to test a blood glucose level according to an embodiment of the present disclosure.

FIG. 8 is a flow chart depicting an exemplary process 800 of using Terahertz waves to test a blood glucose level according to an embodiment of the present disclosure. At 801, a beam of Terahertz waves are generated at the transmitter in an intended energy level and directed onto a target location wherein a subject's eyeball is positioned. It will be appreciated that the present disclosure can be used to test glucose levels in human beings or other suitable subjects, e.g., a pet.

At 802, the incident Terahertz beam is reflected at least partially from the eyeball surface which is covered by a tear layer, and then captured by the receiver. At 803, the detected reflected beam is measured and analyzed, e.g., to determined its E-fields in two polarization orientations. Based on the detection, calculations are performed to determine the reflection characteristics of the eyeball surface with respect to the incident Terahertz beam. The reflection characteristics may be represented by the reflection coefficients in the two polarization orientations or an axial ratio thereof.

At 804, a predetermined correlation between the reflection characteristics of the eyeball and blood glucose level is accessed, which implies a predetermined relationship between tear glucose level and blood glucose level. The correlation may be memory resident and may be determined in any suitable means that is known in the art, e.g., based on clinical and experimental data through a training or other heuristic process in combination with theoretical computation. The correlation may be tuned to a specific subject or a specific category of subjects based on prior testing results.

At 805, provided with the computed reflection characteristics of the tear layer under test, the blood glucose level in the subject is derived according to the predetermined correlation. The test result may then be presented to a user through a display panel and stored in the device for future reference.

Figure 9:
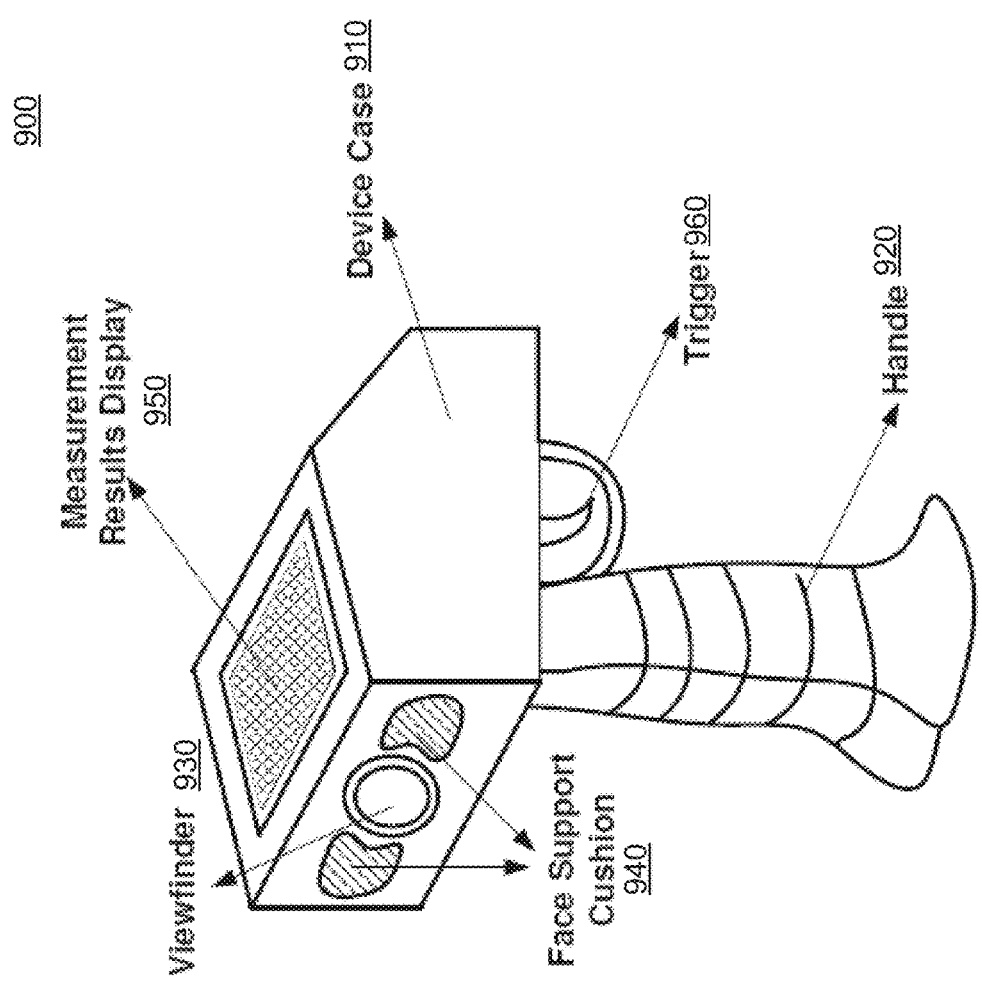
FIG. 9 shows the exterior view of an exemplary glucose sensing device according to an embodiment of the present disclosure.

FIG. 9 shows the exterior view of an exemplary glucose sensing device 900 according to an embodiment of the present disclosure. The device 900 is designed as a handheld device and includes a case 910, a handle 920, a viewfinder 930, facial support cushions 940, a display panel 950 and a trigger 960. For example, for a self-test, a user holds the handle 930 and presses the device 900 against his or her face. The user stares through the viewfinder 930 using one eye and adjusts the eyeball position relative to the device 900 based on perceived locations of the light sources and crosshairs until they are visually aligned, as described with reference to FIGS. 7A and 7B. A position adjustor may be embedded under the cushions 940 to change the distances between the eyeball and the emitter/receiver.

The user can then pull the trigger 960 to effectuate the testing process. The measurement results, e.g., the tear and blood glucose levels, and other related information are displayed on the display device 950. However, it will be appreciated that various other product designs and configurations can be implemented as a glucose sensing device without departing from the scope of the present disclosure.

A sensing device according to the present disclosure may include features to enable a user to conduct a test on another subject who is incapable of conducting a self-set, such as a pet, a child or the like. For example, the positioning information may be made visible to the user conducting the test, and the position adjusting mechanism can be controlled by that user.

Figure 10:
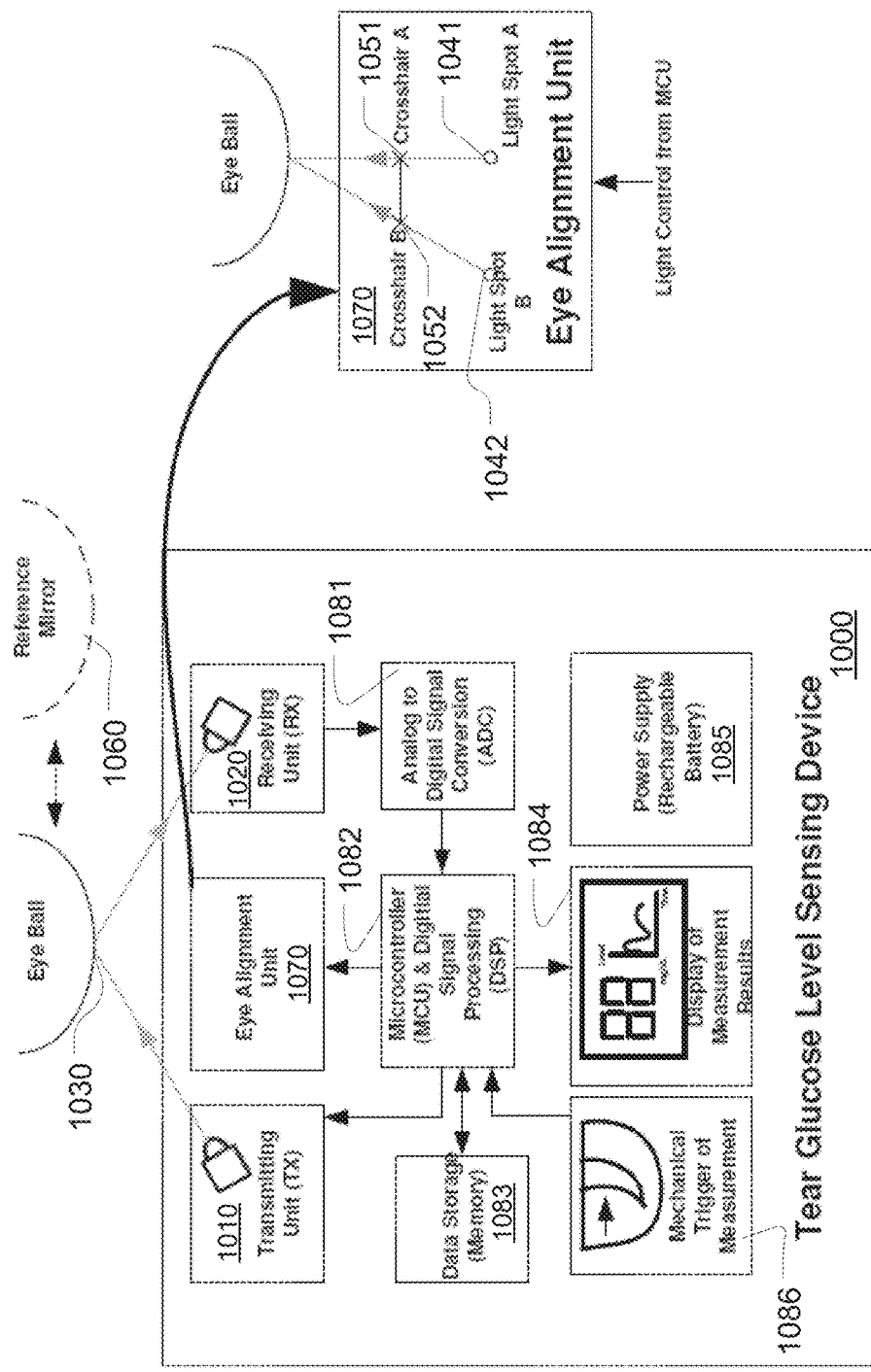
FIG. 10 illustrates the functional modules of an exemplary glucose sensing device according to an embodiment of the present disclosure.

FIG. 10 illustrates the functional modules of an exemplary glucose sensing device 1000 according to an embodiment of the present disclosure. The various modules may be contained in the housing as shown in FIG. 9. The device 1000 includes a transmitting unit (TX) 1010 and a receiving unit (RX) 1020 spaced apart from each other and from the target position where the eyeball 1030 should be located. The device 1000 also includes an eye alignment unit 1070, an analog-digital converter (ADC) 1081, a microcontroller and digital signal processor (DSP) (or collectively "processing logic") 1082, memory 1083, a mechanical trigger 1086 and a display panel 1084 and a power supply 1085.

The eye alignment unit 1070 includes light spots 1051 and 1052 and crosshairs 1041 and 1042 and serves to facilitate a user to adjust the eyeball position to achieve the predetermined angle of incidence and the predetermined distances from the transmitter 1010 and receiver 1020.

When eye alignment is completed, the user can interact with the trigger 1086 to activate the transmitting unit 1010 and the receiving unit 1020. The operation parameters of units 1010 and 1020 may be programmed and controlled by the processing logic 1082, such as frequency, output power, testing duration, emission direction, reflection point location, and etc.

The transmitting unit 1010 emits the Terahertz wave incident on the eyeball surface 1030. The receiving unit 1020 detects at least a portion of the waves reflected from the eyeball surface 1030 and sends signals representing the detected waves to the ADC 1081 for digital conversion. The converted signal is forward to the processing logic 1082 for analysis and computation processing. Accordingly, the processing logic can automatically determine the reflection coefficients or axial ratio of the tear layer covering the eyeball 130 and the resultant blood glucose level according to the predetermine correlation(s). The memory 1083 can store user information, operational parameters of various units in the device, test results, the predetermined correlations, and programs for signal analysis and computations and compiling test results, and etc.

The reference mirror 1060 has known reflection characteristics and is used for calibration as described in greater detail with reference to FIG. 6. In this example, the reference surface has a shape resembling an eyeball. The analysis and computation are similarly performed by the processing logic 1082 based on instructions and data stored in the memory 1083. At the end of each test or in response to a user request, the test result(s) can be displayed on the display panel 1084 in various formats, e.g., a number, a chart or a table.

Each component in the device 1000 can be implemented in any suitable technique that is well known in the art. It will be appreciated that the glucose sensing device may include a range of other components and accessories and performs various other functions. For example, network circuits may be included in the device 1000 such that the test results can be downloaded or remotely transmitted to a computing device.

Figure 11:
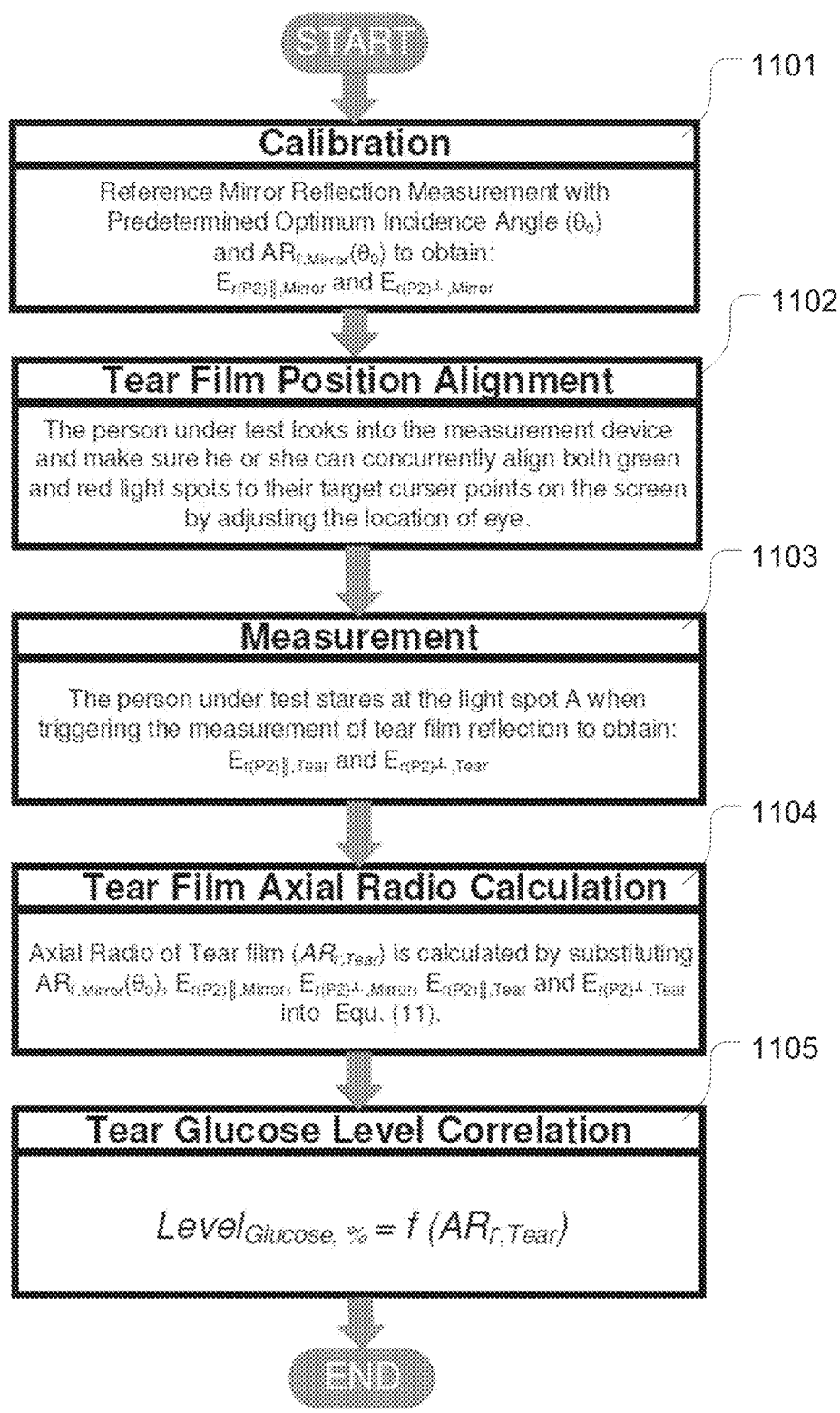
FIG. 11 is a flow chart depicting an exemplary process of using a glucose sensing device as shown in FIG. 10 according to embodiment of the present disclosure.

FIG. 11 is a flow chart depicting an exemplary process 1100 of using a glucose sensing device as shown in FIG. 10 according to embodiment of the present disclosure. At 1101, a calibration process is performed by using reference mirror reflection measurement with predetermined optimum incidence angle and the axial ratio of the reference mirror to obtain $E_{r(P2)\perp,Mirror}$ and $E_{r(P2)\|,Mirror}$. At 1102, a position alignment process is performed. The person under test looks into the viewfinder and adjusts the eye position to ensure he or she can concurrently align both sets of light spots and target cursor points (e.g., a green set and a red set).

At 1103, a glucose measurement is performed. For instance, the person under test stares at the light spot A when triggering the measurement of tear film reflection to obtain the E-fields of the reflected waves at the receiver location P2.

At 1104, the tear film axial ratio is calculated by substituting the E-fields of the reflected waves from the eyeball under test, the reference mirror axial ratio, the E-fields of the reflected waves from the reference mirror into Equation (11). At 1105, the tear glucose level-axial ratio correlation is accessed from memory to obtain the tear glucose level in the person under test. A blood glucose level in the person is further automatically generated based on the tear glucose level-blood glucose level correlation. This determined glucose level is then displayed to the user.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A method of determining glucose levels, said method comprising:
   irradiating first electromagnetic waves onto an eyeball of a subject;
   detecting second electromagnetic waves in two orthogonal polarization orientations produced by said first electromagnetic waves being reflected from said eyeball; and
   determining said glucose level in said subject based on characteristics of said first electromagnetic waves and said second electromagnetic waves and further based on a predetermined correlation between a tear glucose level and a blood glucose level, wherein second electromagnetic waves originate by first electromagnetic waves reflected from a tear film covering said eyeball.

2. The method as described in claim 1, wherein said first electromagnetic waves and said second electromagnetic waves comprise Terahertz waves.

3. The method as described in claim 1, wherein said determining said glucose level comprises:
   determining an axial ratio between reflection coefficients of said tear film with respect to said first electromagnetic waves in two orthogonal polarization orientations; and
   deriving said glucose level according to: a predetermined correlation between said axial ratio and a tear glucose level; and said predetermined correlation between said tear glucose level and said blood glucose level.

4. The method as described in claim 3, wherein said determining said axial ratio comprises:
   determining electric fields of said first electromagnetic waves in said two orthogonal polarization orientations at a first location;
   determining electric fields of said second electromagnetic waves in said two orthogonal polarization orientations based on said detecting at a second location; and
   calculating said reflection coefficients of said tear film based on electric fields of said first and said second electromagnetic waves.

5. The method as described in claim 4, wherein said calculating said reflection coefficients is further based on an angle of incidence of said first electromagnetic waves with reference to said tear film.

6. The method as described in claim 5, wherein said angle of incidence is substantially within a range of 55-85 degrees.

7. The method as described in claim 5 further comprising:
   detecting a position of said eyeball relative to said first location and said second location; and
   sending an indication to said subject for adjusting said position to achieve a predetermined angle of incidence.

8. The method as described in claim 3, wherein said determining said axial ratio comprises:
   determining a reference axial ratio by irradiating said first electromagnetic waves to a reference surface having a known reflection coefficient with respect to said first electromagnetic waves; and
   deriving said axial ratio based on said reference axial ratio.

9. A method of determining a glucose level in a subject, said method comprises:
   at a first predetermined position relative to an eyeball of said subject, irradiating first Terahertz waves onto said eyeball;
   at a second predetermined position relative to said eyeball, detecting second Terahertz waves in two orthogonal polarization orientations produced by said first Terahertz waves being reflected from a tear layer covering said eyeball; and
   automatically determining said glucose level in said subject based on characteristics of said second Terahertz waves relative to said first Terahertz waves and further based on a predetermined correlation between tear glucose level and blood glucose level.

10. The method as described in claim 9 further comprising:
    detecting a position of said eyeball; and
    sending an indication to said subject for adjusting said position to achieve a predetermined angle of incidence of said first Terahertz waves at said eyeball.

11. The method as described in claim 9, wherein said determining said glucose level further comprises:
    determining an axial ratio between reflection coefficients of said tear layer with respect to said first Terahertz waves in two polarization orientations; and
    deriving said glucose level according to a predetermined correlation between said axial ratio and a tear glucose level and further according to said predetermined correlation between said tear glucose level and said blood glucose level.

12. The method as described in claim 11, wherein said determining said axial ratio comprises:
    accessing known characteristics of said first Terahertz waves in said two polarization orientations;
    accessing detected characteristics of said second Terahertz waves in said two polarization orientations; and
    calculating said reflection coefficients of said tear layer based on said known characteristics of said first Terahertz waves and said detected characteristics of said second Terahertz waves.

13. The method as described in claim 11, wherein said known characteristics comprise electric fields in said two polarization orientations.

14. The method as described in claim 11, wherein said determining said glucose level comprises:
  determining a reference axial ratio by irradiating said first Terahertz waves to a reference surface having known reflection coefficients with respect to said first Terahertz waves in said two polarization orientations; and
  calibrating said axial ratio based on said reference axial ratio.

15. A method of detecting a glucose level of a subject, said method comprising:
  irradiating first electromagnetic waves onto an eyeball of said subject;
  determining reflection characteristics in two orthogonal polarization orientations of a tear layer covering said eyeball with respect to said first electromagnetic waves; and
  determining the glucose level in said subject based on said reflection characteristics of said tear layer with respect to said first electromagnetic waves and further based on a predetermined correlation between tear glucose level and blood glucose level.

16. The method as described in claim 15, wherein said determining said reflection characteristics comprises detecting second electromagnetic waves produced by said first electromagnetic waves being reflected from said tear layer.

17. The method as described in claim 15, wherein said first electromagnetic waves and said second electromagnetic waves comprise Terahertz waves.

18. The method as described in claim 15, wherein said determining said reflection characteristics of said tear layer comprises:
  determining an angle of incidence of said first electromagnetic waves at said tear layer;
  determining an axial ratio at said angle of incidence, wherein said axial ratio represents a ratio between reflection coefficients of said tear layer with respect to said first electromagnetic waves in two polarization orientations; and
  automatically deriving said glucose level according to: a predetermined correlation between said axial ratio and a tear glucose level; and a predetermined correlation between said tear glucose level and a blood glucose level.

19. The method as described in claim 16 further comprising determining a reference axial ratio by using a reference surface to reflect said first electromagnetic waves, wherein said determining said axial ratio comprises:
  determining respective electric fields of said first electromagnetic waves and said second first electromagnetic waves; and
  calculating said axial ratio based on said reference axial ratio and said respective electric fields.

* * * * *